US009835532B2

(12) United States Patent
Hall et al.

(10) Patent No.: US 9,835,532 B2
(45) Date of Patent: Dec. 5, 2017

(54) 3D LASER ABLATION TOMOGRAPHY AND SPECTROGRAPHIC ANALYSIS

(71) Applicant: The Penn State Research Foundation, University Park, PA (US)

(72) Inventors: Benjamin Hall, State College, PA (US); Jonathan Lynch, Boalsburg, PA (US); Edward W. Reutzel, State College, PA (US); Galen Lynch, Cambridge, MA (US); Brian T. Reinhardt, Lemont, PA (US)

(73) Assignee: The Penn State Research Foundation, University Park, PA (US)

( * ) Notice: Subject to any disclaimer, the term of this patent is extended or adjusted under 35 U.S.C. 154(b) by 246 days.

(21) Appl. No.: 14/646,250

(22) PCT Filed: Oct. 30, 2013

(86) PCT No.: PCT/US2013/067438
§ 371 (c)(1),
(2) Date: May 20, 2015

(87) PCT Pub. No.: WO2014/070850
PCT Pub. Date: May 8, 2014

(65) Prior Publication Data
US 2015/0323431 A1    Nov. 12, 2015

Related U.S. Application Data

(63) Continuation-in-part of application No. 14/067,502, filed on Oct. 30, 2013, now Pat. No. 9,437,041.
(Continued)

(51) Int. Cl.
*G01N 21/00* (2006.01)
*G01N 1/44* (2006.01)
(Continued)

(52) U.S. Cl.
CPC .................. *G01N 1/44* (2013.01); *G01J 3/00* (2013.01); *G01J 3/2823* (2013.01); *G01N 1/06* (2013.01);
(Continued)

(58) Field of Classification Search
CPC ...... G01N 1/44; G01N 1/06; G01N 2001/045; G01N 2001/2886; G01N 2201/06113; G01J 3/00; G01J 3/2823
(Continued)

(56) References Cited

U.S. PATENT DOCUMENTS 5,689,363 A * 11/1997 Dane ..................... H01S 3/2341
359/334
7,535,565 B1    5/2009 Viertl et al.
(Continued)

FOREIGN PATENT DOCUMENTS

WO    WO-03060477    7/2003
WO    WO-2006037236    4/2006

OTHER PUBLICATIONS

Echlin, M.P. et al., "A New Femtosecond Laser-Based Tomography Technique for Multiphase Materials," Adv. Mater., 23, pp. 2339-2342, 2011.
(Continued)

*Primary Examiner* — Hina F Ayub
(74) *Attorney, Agent, or Firm* — Dinsmore & Shohl LLP (57) ABSTRACT

A laser ablation tomography system includes a specimen stage for supporting a specimen. A specimen axis is defined such that a specimen disposed generally on the axis may be imaged. A laser system is operable to produce a laser sheet in a plane intersecting the specimen axis and generally perpendicular thereto. An imaging system is operable to image the area where the laser sheet intersects the specimen axis.

17 Claims, 4 Drawing Sheets

Related U.S. Application Data (60) Provisional application No. 61/720,144, filed on Oct. 30, 2012, provisional application No. 61/819,882, filed on May 6, 2013.

(51) Int. Cl.
    *G01J 3/28*      (2006.01)
    *G01N 1/06*      (2006.01)
    *G01J 3/00*      (2006.01)
    *G01N 1/04*      (2006.01)
    *G01N 1/28*      (2006.01)

(52) U.S. Cl.
    CPC .............. *G01N 2001/045* (2013.01); *G01N 2001/2886* (2013.01); *G01N 2201/06113* (2013.01)

(58) Field of Classification Search
    USPC .......................................................... 356/72
    See application file for complete search history.

(56) References Cited

U.S. PATENT DOCUMENTS

| | | |
|---|---|---|
| 2001/0016736 A1 | 8/2001 | Lin |
| 2005/0035305 A1* | 2/2005 | Kleinfeld ................ G01N 1/06 250/458.1 |
| 2009/0204110 A1 | 8/2009 | Islam |
| 2012/0184055 A1* | 7/2012 | Kawakami ............ B23K 26/03 438/16 |

OTHER PUBLICATIONS

Targowski P., et al., "Picosecond Laser Ablation System with Process Control by Optical Coherence Tomography," Proc of SPIE 7391, pp. 7391-15, 2009, par. 2.2-2.4.

Fujimoto J., et al., "Optical Coherence Tomography: An Emerging Technology for Biomedical Imaging and Optical Biopsy," Neoplasia, 2(1-2):9-25, par. Guiding Surgical Intervention, Jan. 2000.

International Search Report and Written Opinion for PCT/US2013/067438 dated Feb. 13, 2014.

Search Report Issued in co-pending European application No. 13851579.6 dated Jul. 11, 2016.

Mateo et al., "Surface interaction and chemical imaging in plasma spectrometry induced with a line-focused laser beam", 2002, Elsevier, Spectrochimica Acta Part B, pp. 601-608.

Mateo et al., "Chemical Imaging Using Microline Laser Ablation: Performance Comparison of Gaussian and Flat Top Lasers", 2003, Applied Spectroscopy, vol. 57, No. 3, pp. 343-348.

\* cited by examiner

FIG. 5

3D LASER ABLATION TOMOGRAPHY AND SPECTROGRAPHIC ANALYSIS

This application is the U.S. national phase of PCT/US2013/067438, filed Oct. 30, 2013, which claims priority to U.S. provisional patent application Ser. Nos. 61/720,144, filed Oct. 30, 2012, and 61/819,882, filed May 6, 2013. This application is also a continuation-in-part of U.S. patent application Ser. No. 14/067,502, filed Oct. 30, 2013, which claims priority to U.S. provisional patent application Ser. No. 61/720,144, filed Oct. 30, 2012, the contents of all of which are incorporated herein in their entirety.

STATEMENT OF GOVERNMENT SPONSORSHIP

This invention was made with government support under Grant No. IOS0965380, awarded by the National Science Foundation and from the United States Department of Agriculture under Hatch Act Project No. PEN04372. The government has certain rights in this invention.

FIELD OF THE INVENTION

The present invention relates generally to imaging methods and apparatus and to spectrographic analysis methods and apparatus.

BACKGROUND OF THE INVENTION

A commonly practiced non-destructive technique, confocal microscopy, allows for the imaging of thin planes of focus without background noise interference. These images can be stacked to form a three dimensional model of a subject, but is restricted to sub-millimeter regimes and translucent or transparent matter. Another newly developed method of laser tomography described in M. P. Echlin et al., "A New Femtosecond Laser-Based Tomography Technique for Multiphase Materials," *Adv. Mater.*, 23:2339-2342 (2011), uses a beam oriented perpendicularly to the imaged surface, and removes material at known rates. This method is used for metals and would not work well for samples with varying consistency, density, porosity, and absorption coefficients, as the penetration depth would vary depending on these characteristics.

Other means to image specimens include a microtome method and X-ray microtomography. A microtome (similar in concept to a meat slicer) is used to cut thin sections of a specimen embedded in a paraffin wax substrate which then are transferred to a solution bath to remove excess substrate, then transferred to an imaging device, aligned, acquired, and digitally stacked into a 3D model. X-ray tomography is nondestructive and uses virtual slices taken by a thin X-ray beam and computationally reconstructed. However, this method does not yield compositional data or color, and instead produces a map of the materials' X-ray absorptivity (related to a density profile).

There are a variety of methods for the analysis of composition or molecular analysis of materials or specimens. For example, spectroscopic techniques include Laser Induced Fluorescence (LIFs), Laser Induced Breakdown (LIBs), Hyperspectral imaging and other techniques. However, these techniques are typically practiced as a standalone process with a dedicated apparatus.

SUMMARY OF THE INVENTION

The present invention provides a method for imaging or analysis of a specimen, including its interior, using a laser sheet or beam. The invention incrementally ablates only the desired amount of the specimen and creates a stack of images.

DETAILED DESCRIPTION OF THE INVENTION

The present invention provides a method and apparatus for tomography. It is noted that the term "tomography" often refers to the reconstruction of a specimen through interpretation of the interaction of a "penetrating wave" like X-rays or sound waves within a body. The term "tomography" is used herein to more broadly mean "analysis of three dimensional structure through stacking cross-sectional images", and will refer to the reconstruction of a selected specimen to produce data similar to conventional tomographic techniques.

Embodiments of the present invention provide a high-speed, automated, high resolution, and inexpensive tomographic technique. A working system has been reduced to practice for the specific case of sectioning and 3D reconstruction of plant roots, among other biological specimens. However, the present invention is useful for analysis of other types of materials and specimens, and the herein described embodiments are not intended to limit the scope of the invention.

According to some embodiments, a specimen is moved through a laser "sheet" which ablates a cross section of the specimen. This cross section is imaged using an imaging system. The movement of the specimen, the laser ablation and the imaging may be done in a continuous process or in incremental steps, as will be described in more detail.

Figure 1:
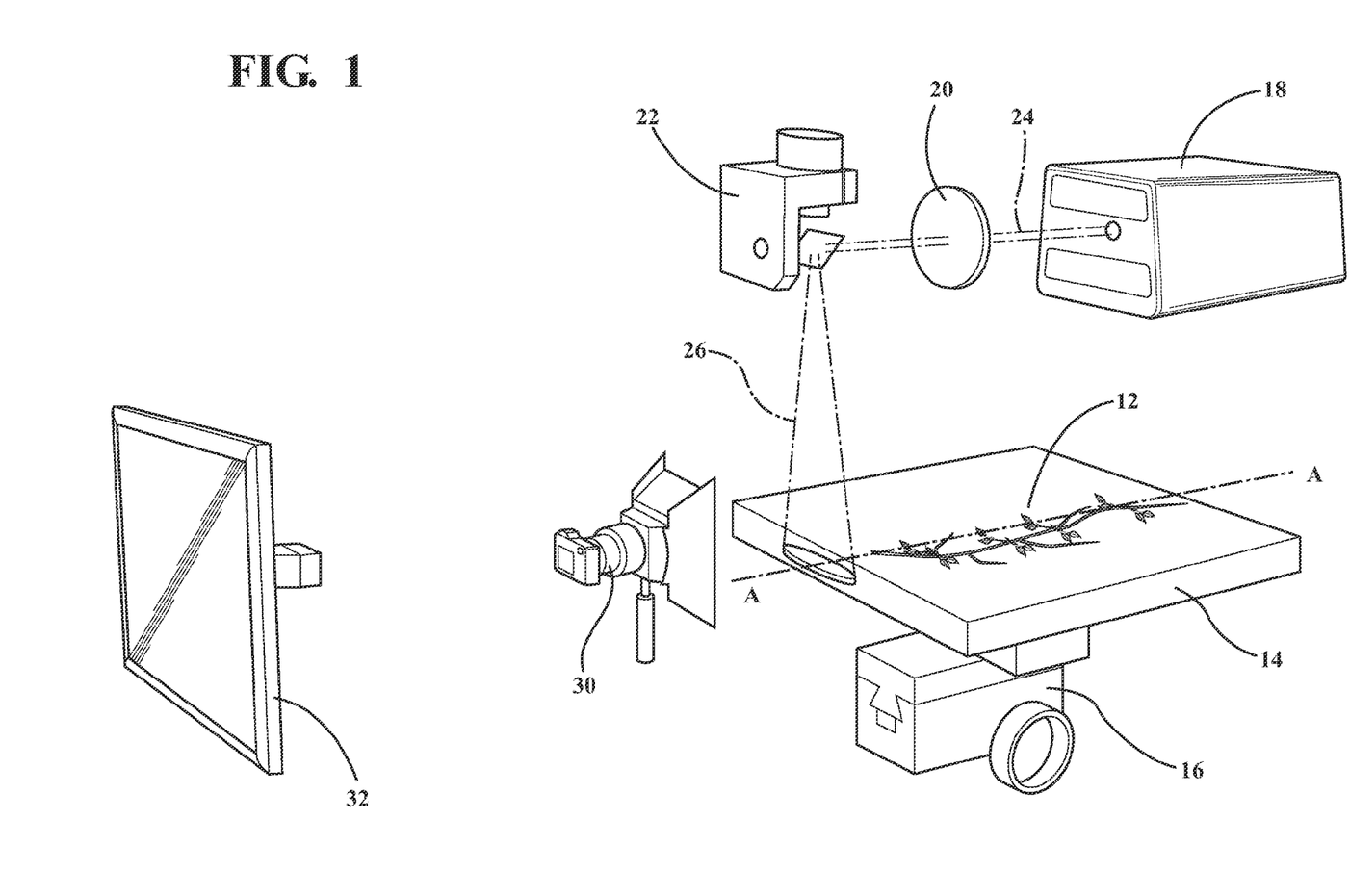
FIG. 1 is a perspective schematic of an embodiment of a 3D laser ablation tomography system in accordance with the present invention.

Referring to FIG. 1, an embodiment of a tomographic imaging system is shown generally at 10. The system may be used to analyze a sample or specimen 12, which is illustrated as a piece of plant material. The specimen 12 is supported on a specimen stage 14. The system may be said to have a specimen axis A-A, with the specimen being positioned generally along this axis. The specimen does not necessarily need to have an axis or be positioned such that its longest dimension is along the axis.

In the illustrated embodiment, the stage moves such that the specimen is moved along the specimen axis. Additional movement may also be provided, such as vertical, side-to-side, and or tilting in various ways. A movement system 16 is used for moving the stage 14. This movement may take a variety of forms. While the stage 14 is illustrated as having a flat surface, the stage may take any form useful for supporting a specimen, and may be considered a specimen support. The specimen may also be partially or completely embedded in a supporting substrate, such as a foam.

A laser "sheet" is provided by a laser system. In this embodiment, a short pulsed laser ($<10^{-6}$ seconds, e.g. a nanosecond, picosecond or femtosecond laser) 18 produces a beam 24 that passes through beam shaping optics 20. A beam director 22 rapidly scans a laser beam along a line to create a "plane" of light, thereby providing the laser sheet 26. The beam director may also take the form of an optical element that splits or reflects the laser beam to create a sheet or sheet-like laser. Such an optical element may be a cylindrical optic. As shown, the laser sheet 26 is perpendicular to the specimen axis A-A. As such, the laser sheet ablates a "slice" of the specimen as the specimen is moved into the sheet.

Short-pulsed lasers are well-suited for a laser system of the present invention because of their high peak-power (irradiance, measured in W/cm$^2$). This high peak power and short pulse duration induce rapid vaporization, or ablation, of the impinged target material with minimal heat effects. This characteristic allows this method to be used on a wide range of materials including ones of porous or inconsistent density.

An imaging system 30 is positioned in alignment with the axis A-A so that the system can image the cross-section of the specimen as it is being ablated. It may also image the specimen before, after, or during ablation, depending on setup of the system. In this embodiment, the imaging system is a magnified Charged Coupled Device (CCD) type camera system, such as a digital SLR camera with a lens focused on the imaging plane defined by the sheet 26. Other types of imaging systems may also be used.

A control system is provided for controlling the imaging device, the stage movement mechanism and the laser system. In the illustrated embodiment, the control system takes the form of a general-purpose computer, represented at 32, modified to perform the control functions.

In this example, reconstruction of a specimen occurs in the following 5 steps:

1. Articulated by mirrors and focusing optics, a rapidly scanned, pulsed laser beam repeatedly sweeps along a line, and creates a planar "sheet of light". The pulse repetition rate of the laser is sufficiently high to allow each subsequent pulse to overlap the prior as the beam sweeps along the line, ensuring a smooth surface. Alternatively, the laser beam may be optically split into a sheet, if the beam has sufficient power.
 2. The imaging device with its focus co-planar with the laser sheet records visual data from a specimen on the opposite side of the laser sheet.
 3. The stage holding the specimen moves the specimen into the laser sheet, either incrementally or continuously.
 4. As the specimen intersects the laser sheet, its camera-facing surface is ablated, exposing the next layer.
 5. This laser-sheet may have a dual purpose—providing a mechanism by way the surface is both ablated and illuminated. This exposure is useful in that the specimen is illuminated only in a plane, and illuminates evenly regardless of porosity, homogeneity, or material type. Alternatively, the system is not limited to using the beam as a source of illumination and in some cases the auto-fluorescence may not be desirable. In such a case, an external beam may be used to excite the sample. This could be necessary when attempting to fluoresce particular molecules.

This method rapidly scans or splits a laser beam along a line to create a "plane" of light. A high magnification camera has its focus set to this plane. A mechanical stage holding the object to be processed slowly pushes the specimen through this focal plane, with its camera-facing surface continuously being ablated. Or, alternatively, the specimen can be moved through the focal plane in discrete steps. The camera captures this sequence of surface removal in HD video or still images. Because the laser beam is irradiating and illuminating just the surface, it is the surface that is imaged. This characteristic enables subsequent post-processing and stacking of images with a computer program with minimal re-editing.

Example System: In one example, a system is used for horticulture specimens using the following components:

A Q-switched, 3rd harmonic, Coherent Avia laser with 30 nanosecond pulses and 355 nanometer wavelength
  GSI Lumonics scanner
  Aerotech stages
  Canon T3i DSLR with a 65 millimeter MP-E 1—5× macro lens
  ImageJ—software from the National Institute of Health A method in accordance with the present invention can produce high-resolution 3D models of nearly any small specimen that can be ablated with a laser. Laser tomography removes small predefined increments of a surface continuously. By adjusting laser parameters, specimens ranging from extremely delicate to much harder materials can be processed. Both a feather and a silicon wafer have been demonstrated on a prototype system.

Using a picosecond or femtosecond laser may be preferred for the sectioning and 3D reconstruction method of the present invention, as it is well understood that the duration of the pulse is on the same order as the thermal diffusion time for many materials, allowing for ablation with minimal thermal effects. This means that specimens that are delicate, fragile, flammable, or highly sensitive to thermal damage can be cleanly sectioned using this process. Additionally, the high irradiance of these pulses means that nearly any material can be ablated and imaged.

The use of a femtosecond or picosecond laser may be preferred for the inventive method. Both investigations and research have shown that there is superior edge quality, reduced thermal impact, increased allowable specimen dimensions (due to higher irradiance and more obtainable ablation thresholds) and wider range of materials that can be processed using ultrafast lasers. Additionally, using shorter wavelengths causes the photons to have bond-breaking energies, which is an athermal process. The use of components like axicon and Fresnel lenses in conjunction with beam-shaping optics can increase the effective depth of field (DOF) and further enhance the process quality.

Referring again to FIG. 1, the laser 18, optics 20 and beam director are illustrated as being positioned above the stage 14 and generally parallel to the axis A-A. As will be clear to those of skill in the art, the components may be rearranged in a variety of ways, such as positioning the laser, optics and director generally perpendicular to the axis A-A and above the imaging system 30, or above the stage 12. Additional positions for each component are possible, including configurations using mirrors or additional optical elements. As one example, the imaging system 30 may be positioned off-axis with images reflected by a mirror or other optical elements.

While the system was described as having the stage 14 move the specimen 12 into the laser sheet 26, alternatively the laser sheet may move while the stage remains stationary, or both may move. Further, the stage and/or laser may tilt, move side to side, or make other adjustments, including ablating the specimen 14 at an angle to the specimen axis A-A. In one example, the stage 14 may rotate such that an outer portion of a specimen is ablated and then the stage is rotated so as to oblate another outer portion of the specimen, such as the opposite end or a side portion. The imaging system may include additional image capturing elements, such as additional cameras imaging from different angles.

Figure 2:
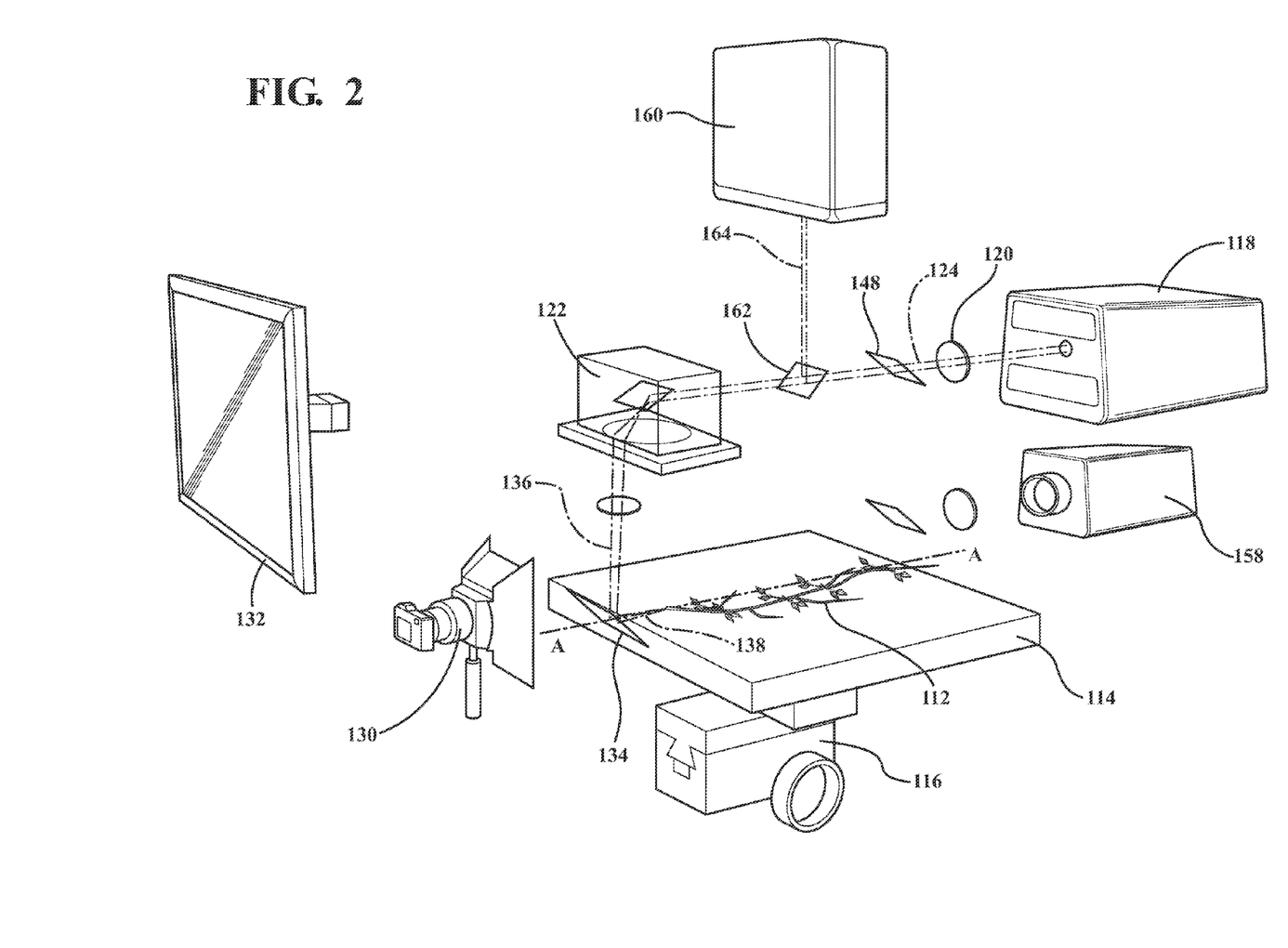
FIG. 2 is a perspective schematic of a 3D laser ablation and spectroscopic analysis system, showing components of a first and second alternative embodiment of the present invention.

Referring now to FIG. 2, a first alternative embodiment of the present invention is shown generally at 110. As with the embodiment of FIG. 1, the alternative embodiment includes a stage 114 for supporting a specimen 112 generally along a specimen axis A-A. A movement system 116 is provided for moving the stage. A laser 118 produces a laser beam 124 which may be shaped by a beam shaping optics 120. In this alternative embodiment, the beam director 122 may be the same as in FIG. 1, but preferably takes a different form, as illustrated, and has additional functionality. In a first mode of operation, the beam director 122 rapidly scans a laser beam along a line to create a plane of light, providing a laser sheet just as in FIG. 1, and ablation and imaging of the specimen 112 proceeds in the same manner discussed above. An imaging system 130 collects images and a control system is represented by the monitor/general purpose computer 132.

Figure 3:
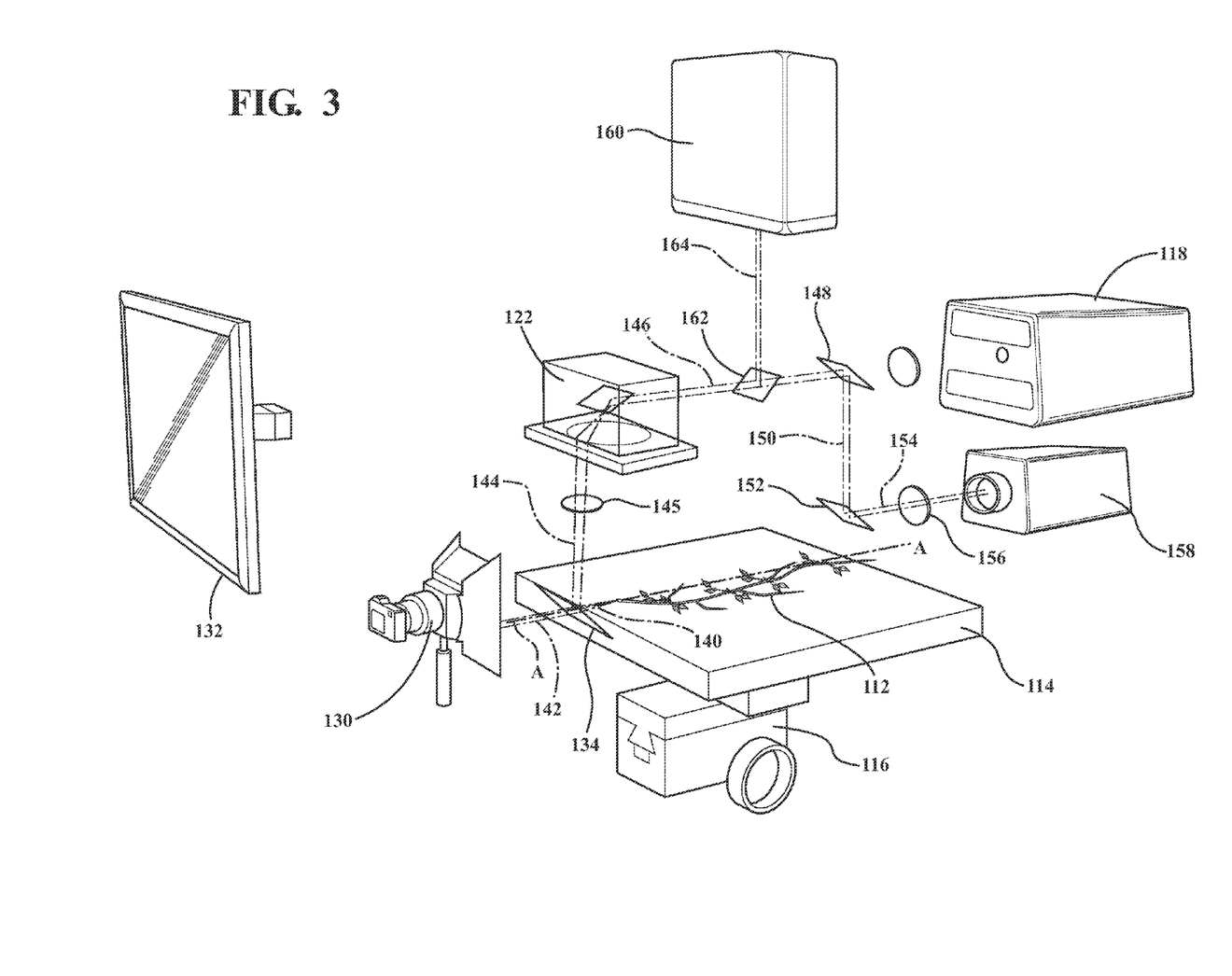
FIG. 3 is a perspective schematic similar to FIG. 2, but showing a light path to a spectrometer.

In a second mode of operation, the system 110 provides for analysis of the specimen, such as analysis by spectrometry. A beam splitter 134 is disposed between the imaging system 130 and the specimen 112. As known to those of skill in the art, a beam splitter is an optical element that reflects a portion of the light hitting the splitter and allows a portion to pass directly therethrough. The beam director 122 directs a laser beam 136 downwardly to this beam splitter 134 and the splitter reflects at least a portion of the laser beam to the end of the specimen 112. This reflected beam 138 is a very narrow beam that hits and ablates a small area of the end of the specimen. This creates a "flash" for spectrographic analysis. FIG. 3 represents the return path for this light. Light from the flash is indicated at 140. This light is generally multi-directional rather than a beam, but the path is illustrated as beam-like since only a portion of the light from the "flash" is analyzed. The light 140 encounters the beam splitter 134. A portion of the light passes through the splitter and is labeled 142. This light 142 may be imaged by the imaging system 130, which allows a determination of the position where the beam 138 "sampled" the specimen and may also be used for analysis, as will be described in more detail below.

An additional portion of the light 140 is reflected by the splitter 134 and becomes beam 144. Optical elements may be provided at any point in the system, such as optical element or lens 145. The optical element is illustrated as also in the path of the laser beam 136 in FIG. 2. The beam 144 passes back through the beam director 122 and is reflected back toward the laser 118. However, this reflected beam 146 encounters another beam splitter 148, which reflects at least a portion of the light 150 down to a mirror 152. The mirror reflects the beam 150 to create beam 154, which may pass through an optical element 156 before entering a spectrometer 158. The spectrometer can determine information about the portion of the specimen that was "sampled" by the laser beam in FIG. 2. In some embodiments, the spectrometer is used to determine the elemental composition of the portion of the specimen that was ablated by the beam 138. The laser 118 produces a short pulse sufficient to create a plasma at the point where the beam 138 hits the specimen 112.

It is noted that the beam splitter 148 is also in the path of the laser beam 124 in FIG. 2, which allows the laser 118 and the spectrometer 158 to share the same light path. As will be clear to those of skill in the art, other arrangements of optical elements, including splitters, lenses, mirrors and other elements, may be used to provide similar functionality. The components of any of the embodiments discussed herein may also be moved around as needed, with appropriate adjustment in the light paths. However, it is preferred that the laser beam for "sampling" the specimen and the analysis light created by the "flash" pass along light paths that are at least partially shared. For example, the laser beam 138 path from the beam splitter 134 to the specimen and the analysis light 140 path are shared, to assure that the an on-axis spectrographic analysis is performed and the spectrometer "sees" the same spot as is ablated by the laser beam 138.

In this embodiment, the laser 118 is preferably of the same type discussed for the embodiment of FIG. 1. It may be a short pulsed laser ($<10^{-6}$ seconds, e.g. a nanosecond, picosecond or femtosecond laser), having high peak-power (irradiance, measured in $W/cm^2$ and short pulse duration to induce rapid vaporization, or ablation, of the impinged target material with minimal heat effects. This characteristic allows this method to be used on a wide range of materials. Alternatively, the laser 118 may be of a different type.

FIGS. 2 and 3 also illustrate components for a second alternative embodiment of the present invention. This alternative includes a second laser 160 which may be of a different type or different power level than the laser 118, to allow for different types of spectroscopy. The second laser 160 may be tunable, pulsed or continuous, and may have a narrow bandwidth (or be filtered to provide a narrow bandwidth) depending on the desired analysis. The second laser may be used in molecular composition analysis. An additional splitter 162 is positioned such that the laser 118 and the second laser 160 can share the same beam path. A laser beam 164 encounters the splitter 162 and is reflected to the beam director 122 and follows the path until it "samples" a portion of the specimen 112. Light from the resulting "flash" is directed back to the spectrometer 158 as was discussed previously. As with the previous embodiment, it is preferred that the laser beam path and the analysis light path are shared or are coaxial such that the spectrometer "sees" the same point ablated by the laser beam.

As will be clear to those of skill in the art, depending on the type and settings of the laser 118 and second laser 160, the system may be used for a variety of spectroscopic techniques. These include, but are not limited to, Laser Induced Fluorescence (LIF), Laser Induced Breakdown (LIB), Ultrafast Transient Absorption, Two-Photon Excitation Spectroscopy, Nonlinear Optical methods, Coherent anti-Stokes Raman Scattering (CARS) and Fourier Transform Spectroscopy. As will also be clear, the spectroscopy may collect light when the laser is actually ablating a small area of the specimen as well as thereafter, allowing time-resolved spectroscopic approaches. Raman spectroscopy measures variations is reflected photon frequencies caused by interference between lattice vibrations and incident monochromatic light. This technique is useful in identifying molecular composition and typically utilizes lasers with wavelengths in the near infrared to ultraviolet. Laser induced breakdown spectroscopy uses short pulse duration lasers typically 200 microjoules or less to ablate a small volume of material. The ablated ions emits light relevant to their elemental composition. Laser induced fluorescent microscopy uses pulsed, continuous, or tunable lasers to excite molecules that reemit light at characteristic wavelengths. Tunable lasers allow scanning through excitation wavelengths to get stronger signals, while pulsed lasers allow time resolved data adding another dimension of identification. All the above use a spectrometer to look and the emitted wavelengths arbitrarily in discrete steps. Any of these approaches may be used with the present invention.

In further embodiments, additional lasers may be provided, with additional optical elements to allow a shared beam path. Alternatively, different lasers may be moved into the position of the second laser 160, depending on the analysis being done. As a further alternative, the analysis light beam 140 may take a different path than the laser beam 138, such as being non-coaxial and analyzing light at an angle to the beam 138. However, this is not preferred.

Figures 4, 5:
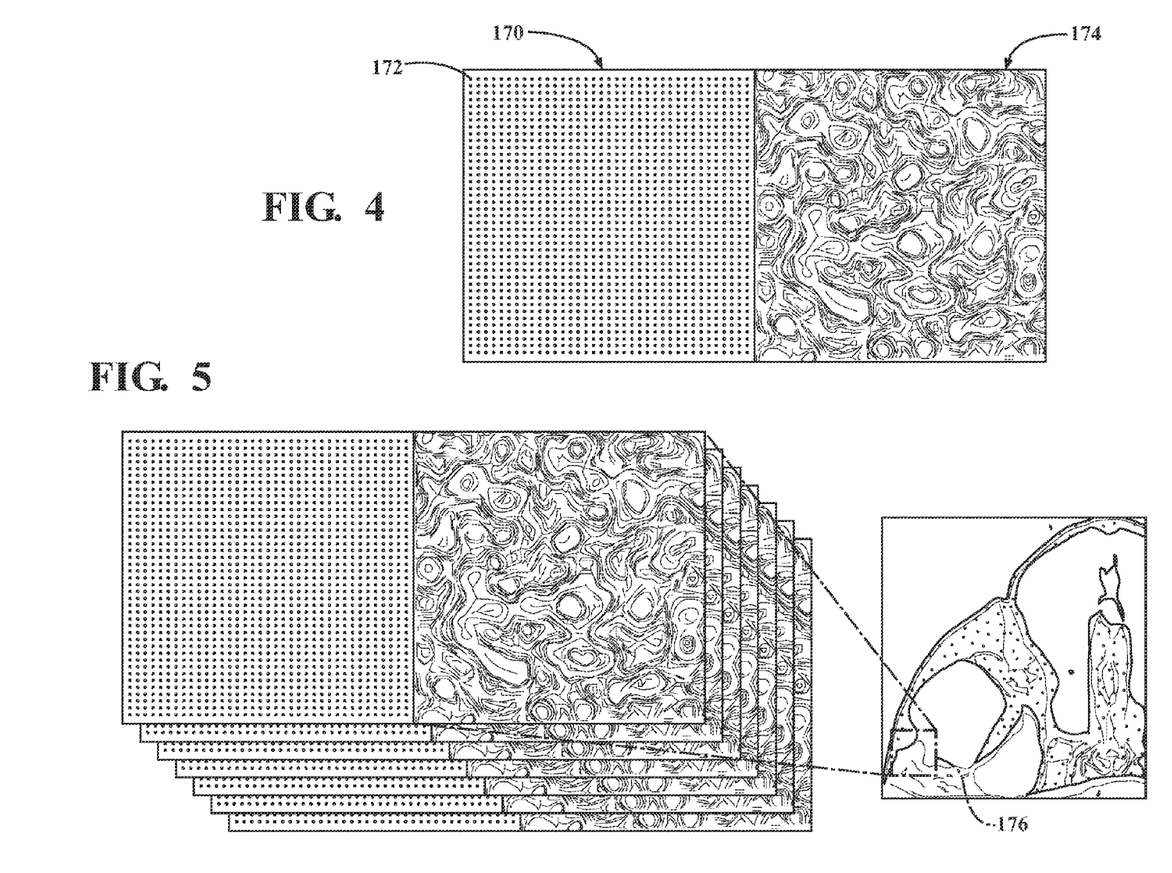
FIG. 4 is a representation of a grid of positions and a spectral map for a portion of a specimen.
FIG. 5 is a representation of a stack of the grids and maps of FIG. 4 and a location from which the maps are taken.

In some versions, the imaging system 130 is used only for visible light image capture. The imaging system captures images of the specimen as layers are ablated by the laser sheet, as was described with respect to FIG. 1. Additionally, the imaging system may capture the location of the "flash" during the analysis stage, with either laser source, so that the control system can determine what location was sampled. Referring to FIG. 4, a grid 170 of dots 172 represents a plurality of points that are sampled during the analysis stage of operation, with each dot representing a "flash". The beam director 122 redirects the laser beam to each of these locations to sample the specimen. The beam director also directs light from this same location back to the spectrometer. Then, another point is sampled. The number, location and sequence of points sampled may depend on the specimen and/or the needs of the user. The data from the imaging system and the spectrometer may then be combined to provide a spectral map, as shown at 174. As shown in FIG. 5, a plurality of grids and maps are created as layers of the specimen are removed. These maps may then be stacked to provide a three dimensional model. As shown in FIG. 5, the illustrated maps may represent only a small area 176 of the specimen, such as an area of particular interest.

The imaging system may provide additional functionality. For example, it may perform multi-spectral imaging by collecting light both in and outside the visible range. The system may include filters, such as a liquid crystal tunable filter (LCTF) to image the specimen at multiple wavelengths during the ablation of the analysis stage, giving additional information on each point sampled.

The system of the present invention may operate in a variety of ways. In one approach, a layer of the specimen is ablated, as was discussed with respect to FIG. 1, and the imaging system images this during and/or after ablation. Then, the system switches to analysis and the laser or second laser are used to ablate a small area and the spectrometer collects light from the resulting "flash". The imaging system collects position information for each flash and may also collect multi-spectral images. Additional points are ablated, as needed. Each of these point ablations removes a very small amount of material, possibly creating tiny pits in the surface. The system then switches back to the first stage, wherein a laser sheet ablates a layer of the specimen. The system continues to switch back and forth, as desired. The system may also switch between which laser is used for analysis either for different points or different layers. The user may set the system to remove multiple layers between each analysis step or may analyze after each layer is removed.

As will be clear to those of skill in the art, the illustrated and discussed embodiment of the present invention may be altered in various ways without departing from the scope or teaching of the present invention. As one non-limiting example, mirrors may be used to move the imaging device off axis, for packaging or other reasons. As another non-limiting example, fiber optics may be used to route light, such as to the spectrometer. It is the following claims, including all equivalents, which define the scope of the invention.

We claim:

1. A laser ablation tomography and spectroscopic analysis system, comprising:
    a specimen stage for supporting a specimen to be imaged, a specimen axis being defined from a fore end of the specimen to an aft end of the specimen;
    a laser system operable to produce a laser sheet in an imaging plane intersecting the specimen axis substantially perpendicular thereto, the laser sheet operable to ablate a cross-sectional slice of the specimen at the imaging plane thereby exposing a cross-sectional surface of the specimen at the imaging plane;
    an imaging system operable to image the cross-sectional surface of the specimen being ablated during, before or after the laser sheet ablates the cross-sectional slice of the specimen; and
    a spectrometer operable to capture light from the cross-sectional surface of the specimen.

2. A laser ablation tomography and spectroscopic analysis system in accordance with claim 1, further comprising:
    a movement system operable to cause relative movement between the specimen stage and the laser sheet along the specimen axis.

3. A laser ablation tomography and spectroscopic analysis system in accordance with claim 2, further comprising:
    a control system operable to control the imaging system and the movement system.

4. A laser ablation tomography and spectroscopic analysis system in accordance with claim 1, wherein the imaging system comprises a camera with a Charged Coupled Device (CCD).

5. A laser ablation tomography and spectroscopic analysis system in accordance with claim 1, wherein:
    the laser system is operable in a first mode of operation to produce the laser sheet and further operable in a second mode of operation to produce a laser beam for irradiating a small area of the specimen,
    the spectrometer arranged to capture light from the irradiated area when the laser system operates in the second mode of operation.

6. A laser ablation tomography and spectroscopic analysis system in accordance with claim 5, wherein the laser system further comprises beam shaping optics disposed such that the beam from the laser passes therethrough.

7. A laser ablation tomography and spectroscopic analysis system in accordance with claim 5, wherein:
    the laser beam from the laser system in the second mode of operation is generally perpendicular to the plane defined by the laser sheet.

8. A laser ablation tomography and spectroscopic analysis system in accordance with claim 5, wherein:
    the laser system comprises a laser operable to produce a laser beam and a beam director operable in the first mode of operation to rapidly scan the laser beam so as to create the laser sheet and in the second mode of operation to position the laser beam for irradiating the small area.

9. A laser ablation tomography and spectroscopic analysis system in accordance with claim 8, wherein:
    the laser system further comprises at least one beam splitter disposed between the specimen stage and the imaging system, the laser beam in the second mode of operation hitting the beam splitter.

10. A laser ablation tomography and spectroscopic analysis system in accordance with claim 5, wherein:

the imaging system is further operable to capture a location of the irradiation when the laser system is in the second mode of operation.

11. A laser ablation tomography and spectroscopic analysis system in accordance with claim 5, wherein:
the laser system comprises a first laser operable to produce a first laser beam and a second laser operable to produce a second laser beam,
the laser system further comprising a beam director operable in the first mode of operation to rapidly scan the first laser beam so as to create the laser sheet and in the second mode of operation to position the second laser beam for irradiating the small area.

12. A laser ablation tomography and spectroscopic analysis system in accordance with claim 11, further comprising:
a beam splitter positioned where the laser beams from the lasers intersect so that the laser beams share a beam path after the beam splitter.

13. A laser ablation tomography and spectroscopic analysis system in accordance with claim 11, wherein:
the first laser is a femtosecond or picosecond laser.

14. A laser ablation tomography and spectroscopic analysis system in accordance with claim 11, wherein:
the second laser is selected from the group consisting of a short pulsed tunable laser and a continuous laser with narrow bandwidth.

15. A method for laser ablation tomography and spectroscopic analysis, comprising the steps of:
providing the laser ablation tomography and spectroscopic analysis system of claim 1;
positioning a specimen on the specimen stage such that a portion of the specimen may be ablated;
ablating the specimen with the laser sheet;
imaging the specimen where it was ablated;
irradiating a portion of the specimen with the laser beam;
analyzing the irradiated portion of the specimen with the spectrometer; and
repeating the positioning, ablating, irradiating, imaging and/or analyzing steps.

16. A method in accordance with claim 15, wherein:
the imaging step is performed during the ablating with the laser sheet step.

17. A laser ablation tomography and spectroscopic analysis system in accordance with claim 1, wherein the laser system is operable to produce a laser beam to irradiate a portion of the specimen by illuminating or ablating the portion of the specimen.

* * * * *